United States Patent [19]

Fersch

[11] Patent Number: 5,380,350
[45] Date of Patent: Jan. 10, 1995

[54] METHODS OF MAKING GRANULAR WATER SOLUBLE OR HYGROSCOPIC AGRICULTURAL FORMULATIONS

[75] Inventor: Ken Fersch, Apex, N.C.

[73] Assignee: BASF Corporation, Parsippany, N.J.

[21] Appl. No.: 968,926

[22] Filed: Oct. 30, 1992

[51] Int. Cl.⁶ ............................................ H01N 25/12
[52] U.S. Cl. ................... 71/64.03; 71/64.04;
  71/64.05; 71/64.12; 71/DIG. 1; 504/116;
  504/222; 504/248; 504/280; 504/323; 504/324;
  504/344; 514/951; 427/212; 427/213;
  427/213.31
[58] Field of Search .................. 504/248, 116;
  71/DIG. 1, 64.03, 64.04, 64.05, 64.12; 427/212,
  213, 213.31

[56] References Cited

U.S. PATENT DOCUMENTS

| | | | |
|---|---|---|---|
| 3,905,798 | 9/1975 | Zech et al. | 504/181 |
| 4,338,118 | 7/1982 | Krumklans | 71/76 |
| 4,826,531 | 5/1989 | Anthony et al. | 71/94 |
| 5,165,934 | 11/1992 | Wada et al. | 424/409 |
| 5,180,420 | 1/1993 | Katayama et al. | 504/116 |
| 5,204,119 | 4/1993 | Shiobara et al. | 424/489 |

FOREIGN PATENT DOCUMENTS 2238960  6/1991  United Kingdom.
WO89/00079  1/1989  WIPO.

*Primary Examiner*—Richard L. Raymond
*Assistant Examiner*—B. Bembenick
*Attorney, Agent, or Firm*—Nixon & Vanderhye

[57] ABSTRACT

The present invention provides methods of making hygroscopic pesticidal salt formulations in the form of dispersible granules.

28 Claims, No Drawings

METHODS OF MAKING GRANULAR WATER SOLUBLE OR HYGROSCOPIC AGRICULTURAL FORMULATIONS

BACKGROUND OF THE INVENTION

1. Field of the Invention

The present invention relates to methods for making dispersable granular forms of salts of water soluble or hygroscopic pesticidal compounds.

2. Background of the Prior Art

Granular formulations of pesticides tend to be safer in application and environmentally, as they are more easily handled by the farmer. Dry, flowable formulations of silica and oil soluble pesticides are known. These formulations are generally adsorbed onto a solid carrier, milled and then granulated. However, this technique is generally unacceptable when attempted for use with water soluble or hygroscopic agricultural products.

The plant growth regulator, known trivially as mepiquat chloride, is a water soluble pesticidal salt and is generally used to control various aspects of cotton boll growth. See, for example, Khafaga, Angew. Botanik 57, 257–265 (1983); Sawan et al., J. Agronomy & Plant Science, 154, 120–128 (1985); U.S. Pat. Nos. 3,905,798 and 4,447,255.

As an example, mepiquat chloride has a high water solubility, in general, more than about 600 g/L. The substance is very hygroscopic, readily absorbing moisture from humid air, so that the dry powder can turn to liquid when exposed to ambient humid air. Additionally, the solid material cakes rapidly in storage and sticks to container surfaces, even when initial water contents below 0.5%. These properties make it extremely difficult to granulate and disperse mepiquat chloride, for example.

There is a need for methods of making dispersable, granular formulations for water soluble or hygroscopic pesticidal compounds which maintain the biological activity of the water soluble or hygroscopic pesticidal compound and eliminate milling.

SUMMARY OF THE INVENTION

It has been discovered that dispersible granular formulations of water soluble or hygroscopic pesticidal compositions can be produced. The method of making these dispersible granular formulations uses highly absorbent solids to form a stable, dry product without the need for a milling step to attain an effective particle size of the dispersed product.

The method of the present invention involves adsorbing the pesticide onto a highly absorptive carrier. Thereafter, the adsorbed pesticide/carrier composition is granulated by granulating means well known in the art. The granulated pesticide/carrier composition is then dried and the composition is sized to remove any oversize fines.

The particularly preferred pesticides of the present invention are salts of water soluble or hygroscopic pesticides. These preferred pesticides include, for example, plant growth regulators, including the group consisting of 1,1-dimethyl-3,4-dehydropiperidinium bromide, 4-chloro-1,1-dimethyl piperidinium bromide, 1,1-dimethylhexahydro pyridazinium bromide, and 1,1-dimethylpiperidinium chloride; and herbicides such as sodium bentazon and sodium acifluorifen.

It is an object of the present invention to provide methods of making dispersable granular forms of salts of water soluble or hygroscopic pesticidal compounds.

This and other objects of the present invention will be more fully understood from the following description of the invention.

DETAILED DESCRIPTION PREFERRED EMBODIMENTS

As used herein, the term "agriculturally acceptable" includes agricultural, industrial and residential use.

As used herein, the terms "pesticide(s)" or "pesticidal" include plant growth regulators, insecticides, acaricides, nematocides, fungicides, miticides, pesticides, herbicides, fungicides, pesticides, algicides, bactericides and mollusicides.

As used herein, "plant growth regulator(s)" (hereinafter abbreviated as "PGR") or "regulation" includes the following plant responses: inhibition of cell elongation, for example reduction in stem height and internodal distance, strengthening of the stem wall, thus increasing the resistance to lodging; compact growth in ornamentals for the economic production of improved quality plants; promotion of better fruiting; increasing the number of ovaries with a view to stepping up yield; promotion of senescence of the formation of tissue enabling fruit to absciss; defoliation of nursery and ornamental bushes and trees for mail-order business in the fall; defoliation of trees to interrupt parasitic chains of infection; hastening of ripening, with a view to programming the harvest by reducing the harvest to one to two pickings and interrupting the food-chain for injurious insects.

As used herein, the formulations of the present invention may be used to form both package and tank mix compositions.

The method of the present invention involves adsorbing the pesticide onto a highly absorptive carrier. Thereafter, the adsorbed pesticide/carrier composition is granulated by granulating means well known in the art. The granulated pesticide/carrier composition is then dried and the composition is sized to remove any oversize fines.

The present preferred invention uses salts of water soluble or hygroscopic pesticidal compounds comprising an agriculturally and plant growth regulating effective amount of a the hygroscopic pesticidal compound, and more preferably, a salt of a plant growth regulator (PGR) or a salt of a herbicide.

Specific preferred examples include N,N-dimethylpiperidinium salt, bentazon salt or sodium acifluorifen in a dry flowable highly concentrated powder.

Preferred PGRs include salts of the formula:

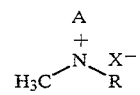

where R is methyl or ethyl; X is the anion of an inorganic or organic, but not phytotoxic acid, preferably bromide or chloride, and A is a chain of 4 or 5 methylene groups, which chain may be substituted by chloro, bromo, methyl, chloromethyl, bromomethyl, hydroxymethyl, and methylene, or which chain containing one or two double bonds, or A is the chain —(CH$_2$)$_n$—NH—, where n is 3 or 4, disclosed in U.S. Pat. No. 3,905,798 and hereby incorporated by reference.

Preferred specific examples of PGRs include 1,1-dimethyl-3,4-dehydro-piperidinium bromide, 4-chloro-1,1-dimethyl- piperidinium bromide, 1,1-dimethylhexahydropyridazinium bromide and 1,1-dimethylpiperidinium chloride. The most preferred plant growth regulator is 1,1-dimethyl-piperidinium chloride, also known as N,N-dimethylpiperidinium chloride or mepiquat chloride. This product is commercially available under the registered trademark Pix ® (BASF AG, Germany).

Preferred herbicides include, for example, the sodium salt of bentazon (available commercially as BASAGRAN from BASF Corporation), the sodium salt of acifluorifen (available commercially as BLAZER from BASF Corporation), the sodium salt of sethoxydim, the dimethylamine salts of 2,4-D, difenzoquat methyl sulfate (commercially available as AVENGE from American Cyanamid), and the like.

The granules of the present invention may be prepared by adsorbing the active ingredients onto highly absorptive solid carriers. Thereafter, one may add any optional ingredients or additives. The wet powder is then granulated by means well known in the art, including, but not limited to, extrusion, pan granulation and Schugi agglomeration.

The process of the instant invention eliminates the need for a milling step. The elimination of this step reduces the cost and time of production, as well as avoids worker exposure to respirable dust associated with most commercial milling processes.

The granule size is determined by the end application, however, it is preferred that the granule diameter be about 0.7 mm to about 1.5 mm for extrusion and about −8 to about +30 mesh for other granulation techniques.

The wet granules are then dried by means well known in the art, including, but not limited to oven drying and fluid bed drying. Drying generally occurs after about 4 to about 60 minutes.

After the drying step is completed, the granules are then sized to eliminate fine and dust. The final granule particle size is preferred to be a mixture of about <1.0 wt % +8 mesh, <3.0 wt % −30 mesh and <0.2 wt % −100 mesh. The preferred median dispersed particle diameter size is about <40 micron after 5 minutes with dissolution without sonics. The loose bulk density is about 21 to 31 lb/cu ft or 0.34 to 0.50 g/ml. A packed bulk density is preferred to be about 23 to 33 lb/cu ft or 0.36 to 0.54 g/ml.

When the final granules are suspended, they are preferred to have a solids suspendability content of greater than about 50%, by standard test means of the art. When the granules are suspended the active pesticide present should be greater than about 90%. The final granule has a preferred nominal diameter of about 1.5 mm. It is preferred to have minimal extraneous materials or contaminants in the product.

Examples of absorptive solid carriers may be synthetic or natural and include, for example, synthetic silicas, mineral earths such as silicic acid, silica gels, silicates, talc, kaolin, Attaclay, limestone, lime, chalk, bole, loess, clay, dolomite, diatomaceous earth, synthetic calcium silicate (available commercially as Microcel E), calcium sulfate, magnesium sulfate, magnesium oxide, and mixtures thereof.

The most preferred absorptive solid carrier is synthetic calcium silicate. The synthetic calcium silicate provides significant absorption of the active ingredient onto the carrier with minimal agglomeration. This combination has superior tolerance of the varying shear intensity during agitation in the end use tank.

In general, the formulations of the present invention contain from about 0.1 to about 95%, and preferably from about 5 to about 50% by weight of active ingredient.

The ratio of carrier to active ingredient (pesticide plus granulation water) is about 0.1 to about 2.0, and more preferably about 0.2 to about 1.0.

While the ratios of the concentrations of the various components of the present invention hereinafter suggested, those skilled in the art will recognize that minor variations may be necessary to accommodate particular characteristics of acceptable actives which may be employed in this invention.

Optionally, dispersing agents may be incorporated into the granule in the same manner as the active. Suitable examples of dispersing agents include nonionic or anionic surfactants.

Specific suitable examples include condensed sulfonate sodium salt (available commercially as Morwet D-425 from Desoto, Inc., Des Plaines, Ill.), polyvinylpyrrolidone (available commercially as Polyplasdone XL-10 from International Specialty Products, Wayne, N.J. or as Kollidon Cl M-10 from BASF Corporation, Parsippany, N.J.), organosilicones such as polyalkylene oxide modified polydimethylsiloxane (available commercially as Silwet 7607 from Union Carbide Corporation), alcohol ethoxylates such as 2,6,8-trimethyl-4-nonyloxypolyethyleneethanol (available commercially as Tergitol TMN6 from Union Carbide Chemicals and Plastics Company, Inc.), lignosulfonic acids such as Reax 88A or lignosulfonic acid formulations with wetting agents such as Reax 45DTC (both available commercially from Westavco, Charleston Heights, S.C.).

The most preferred dispersing agents are lignosulfonic acid formulations or condensed sulfonate sodium salts. It is most preferred to use a mixture of either of lignosulfonic acid formulations or condensed sulfonate sodium salts with polyvinylpyrrolidone (PVP). The dispersing agent may be present in the present invention in an amount of from 0 to about 15.0%, by weight and more preferable about 0.5 to about 15.0%, by weight. The PVP dispersing agent is preferably present in an amount of 0.0 to 5.0%, by weight, and more preferably in an amount of about 0.2 to about 2.0%, by weight.

A wetting agent may also be used in the present invention. Suitable examples include nonionic and anionic surfactants, and more specifically, mixtures of alkyl carboxylates and sulfonated alkyl naphthalene, and their sodium salts (available commercially as Morwet EFW from DeSoto, Inc., Des Plaines, Ill.). A wetting agent is preferably present in an amount of about 0.0 to 10.0%, by weight, and more preferably about 0.5 to about 10.0%, by weight.

In addition, absorptive filler/binders may be incorporated into the composition of the present invention. Suitable examples of absorptive filler/binders include micas or clays such as kaolin, attapulgite, montmorillonite or bentonite, and the like.

The most preferred filler/binder is delaminated kaolin (available commercially as Englehard ASP-NC from Englehard Chemical Corp.). Filler/binders may be present in the present invention in an amount of from 0 to about 60% by weight, and more preferably, from about 1.0 to about 40%, by weight.

In addition to the above-described components, the compositions of the present invention may also include other ingredients or adjuvants commonly employed in the art.

Examples of such ingredients include drift control agents, defoaming agents, preservatives, surfactants, fertilizers, phytotoxicants, adherents, trace elements, synergists, antidotes, mixtures thereof and other such adjuvants well known in the plant growth regulator art.

However, it is preferred to employ the compositions of the present invention along with sequential treatments with these other components for optimal effect.

The formulations of the present invention have good storage stability.

The compositions of the present invention may be applied to above ground portions of plants. The application of liquid and particulate solid compositions to above ground portions of plants may be carried out by conventional methods, for example, boom and hand application, including sprayers or dusters. The compositions may be applied aerially as a spray, if desired. The mixtures of the present invention are preferably used in the form of aqueous dispersions. The mixtures are applied in a conventional manner, for example, by spraying, atomizing, watering or disinfecting seed.

The forms of application depend entirely on the purpose for which the compositions are being used. In any event, they should ensure a fine distribution of the active ingredients in the composition.

The above plant growth regulator formulation may then be dispersed in water and sprayed onto plants according to the method of the present invention.

The action of the compositions of the present invention are optimal even at low application rates. For a given composition, the skilled artisan will readily arrive at a composition having the optimum ratio of the ingredients by routine experimentation.

The following examples serve to illustrate the invention and should in no way be construed as limiting the scope thereof.

EXAMPLES

The following components were used in the following examples:

| Raw Material | at 25° C. | Supplier | w/w |
| --- | --- | --- | --- |
| Mepiquat Cl. Tech | Liquid | BASF Corp. | x g/kg |
| Microcel E | Powder | Manville Corp. | 293 g/kg |
| Morwet EFW | Powder | Witco Corp. | 30 g/kg |
| Morwet D-425 | Powder | Witco Corp. | 50 g/kg |
| Agrimer ATF | Powder | GAF Chemicals Corp. | 10 g/kg |
| Barden Fine Clay | Powder | J. M. Huber Corp. | 250 g/kg |
| Residual Water | Liquid | Tap | 15 g/kg | where x gives about 350 g/kg active Mepiquat Chloride.

At 1.5% water in the product described above, the formulation ai will be 35.2%. If the product moisture reaches the upper spec of 2 wt %, the formulation ai will then be at label of 35.0 et %.)

Mepiquat Chloride Tech (available commercially as PIX ® Manufacture's Concentrate 60 from BASF Corporation) was used. It is a yellow, water solution of negligible vapor pressure and is not combustible. Synthetic calcium silicate (Microcel E, a crystalline silica free (CSF) form of diatomaceous earth) was used as a carrier. A mixture of alkyl carboxylate and sulfonated alkyl naphthalene, sodium salt (Morwet EFW) was used as a wetting agent. A binder and dispersing agent of condensed naphthalene sulfonate sodium salt (Morwet D-425) was also used.

Feed Preparation—Batch

The batch size was computed to give a full charge to the blender to be used. Weighed amounts of each solid raw material were charged to the blender. A stainless steel ribbon blender, paddle mixer, kneader, or other suitable blender was used for homogenizing the materials. After liquids (active and granulation water) were added to the batch, it contained about 34% water and the bulk density of the extruder feed would go up to around 34 lb/cu ft. The blender was equipped with spray nozzles for the technical and for water and have appropriate air extraction. Blend time for a properly filled ribbon or paddle mixer was about 20 minutes. The Microcel E and then the clay were added first and second to the blender.

Weighed amounts of mepiquat chloride technical and water are added to a polyethylene or stainless steel liquid mixing vessel with agitator, and stirred for 5 minutes. This is sprayed onto the mixing solids, after the solids were premixed. Blend time after all the liquid is added was about 5 to 10 minutes.

Feed Preparation—Semi-Continuous

Solid raw materials are blended per the feed preparation described above. A solution of mepiquat chloride and water using were prepared using about half of the calculated, theoretical amount of water. This mixture was stirred for about 5 minutes. The blended solids were metered to a continuous mixer with a gravimetric feeder.

For this rate of solids, the liquids rate was calculated to give a dry product of about 35.2 wt % mepiquat chloride. A positive displacement metering pump was calibrated to deliver this flow rate. The liquid is appropriately sprayed onto the mixing solids in the continuous blender.

A second liquid stream of water alone was also sprayed onto the mixing solids in the continuous blender. This stream was used to control the consistency of the wet solids which were charged to the extruder. Its rate was adjusted as needed.

Extrustion and Drying

The solids wetted with ai and water were fed to a Luwa basket type extruder of appropriate size. The product was extruded with a 1.5 mm die. The extrudate was discharged to a stainless steel fluid bed dryer where the water content was reduced to below 2 wt %. Drying air temperatures up to 75° C. were employed without damage to the product.

Screening

A vibratory screen apparatus equipped with 8 and 30 US Sieve screens to separate oversize and fines from the product were used. The product was screened to about −8 in a +30 mesh US Sieve. The +8 oversize fraction was extremely small and was reworked into the system manually. The −30 fines ranged from 2 to 8 wt % of the dryer discharge. These may be added to dry solids blender (along with any recycled dust). An adjustment in the water rate may be needed and is why the semi-continuous process is preferred.

Hygroscopicity Tests

Hygroscopicity tests were conducted which showed that the product absorbed water at a rate dependent upon the relative humidity. At 76% relative humidity, the product gained only 5 wt % after 2 hours exposure and completely maintained its granular structure.

PARTICLE SIZE DETERMINATION

The method of evaluating performance of the formulation was to determine the median dispersed particle size (diameter). A Cilas Granulometre Model 715 was used. A sample was added to water, which is stirring at about 50% power. After about five minutes, the median particle size was determined. The sample was then sonicated for thirty seconds and another median particle size was determined. Sonication or use of sonic energy provides very significant agitation.

The most preferred formulations include the ones with substantially the same median dispersed particle size values for both pre- and post-sonication.

All of the following formulations were tested according to the above procedure.

TABLE I

| Formulation No. | 1 | 2 | 3 | 4 | 5 | 6 |
|---|---|---|---|---|---|---|
| Mepiquat Cl Tech | 34.5 | 35.2 | 35.2 | 35.5 | 35.4 | 35.2 |
| Morwet EFW | 3.0 | 2.0 | 3.0 | 3.0 | 3.0 | 3.0 |
| Morwet D-425 | 9.8 | 10.0 | 5.0 | 10.0 | 5.0 | — |
| Reax 45DTC | — | — | — | — | — | 5.0 |
| PVP | — | 2.0 | — | — | 1.0 | 1.0 |
| Sipernat 50 S | 28.5 | 29.3 | 29.3 | — | — | — |
| Microcel E | — | — | — | 29.0 | 29.2 | 29.3 |
| Barden Fine | 22.6 | 20.0 | 27.5 | 21.0 | 24.9 | 25.0 |
| ASP-NC | — | — | — | — | — | — |
| Residual Water | 1.5 | 1.5 | 1.5 | 1.5 | 1.5 | 1.5 |
| MEDIAN PARTICLE SIZES IN MICRONS | | | | | | |
| No Sonics | 86 | 56 | 46 | 34 | 27 | 19 |
| Sonics | 11 | 10 | 9 | 15 | 16 | 17 |
| LONG TERM STORAGE STABILITY | | | | | | |
| 6 Mo, 40° C., in 8030 PVA | | | | | 74/17* | |
| 1 Yr, 25° C. in HDPE Bottle | | | | | 51/16* | |

*No Sonics/Sonics

| Formulation No. | 7 | 8 | 9 | 10 | 11 | 12 |
|---|---|---|---|---|---|---|
| Mepiquat Cl Tech | 35.2 | 35.2 | 35.2 | 35.2 | 35.2 | 35.2 |
| Morwet EFW | 3.0 | 3.0 | 3.0 | 3.0 | 3.0 | 3.0 |
| Morwet D-425 | 5.0 | 5.0 | 5.0 | — | 5.0 | — |
| Reax 45 DTC | — | — | — | 5.0 | — | 5.0 |
| PVP | 1.0 | 1.0 | 1.0 | 1.0 | 1.0 | 1.0 |
| Sipernat 50 S | — | — | — | — | — | — |
| Microcel-E | 29.3 | 29.3 | 29.3 | 29.3 | 22.3 | 22.3 |
| Barden Fine | 25.0 | — | 25.0 | — | — | — |
| ASP-NC | — | 25.0 | — | 25.0 | 32.0 | 32.0 |
| Residual Water | 1.5 | 1.5 | 1.5 | 1.5 | 1.5 | 1.5 |
| MEDIAN PARTICLE SIZES IN MICRONS | | | | | | |
| No Sonics | 24 | 20 | 33 | 23 | 18 | 16 |
| Sonics | 16 | 17 | 16 | 16 | 15 | 16 |
| LONG TERM STORAGE STABILITY | | | | | | |
| 1 Mo, 50° C., in 8030 PVA Film | | | | | | |
| Sonics | 15 | | 17 | 15 | 16 | |
| No Sonics | | 58 | | 27 | 24 | 18 |
| 1 Mo, 50° C. in KB PVA Film | | | | | | |
| Sonics | | 16 | | | 15 | 16 |
| No Sonics | | 51 | | 25 | | 17 |

The following examples used the methods described in the above examples but used salts of water soluble pesticides. As can be seen from the sonic testing, the pesticidal formulations generated active products.

Example 2: Acifluorifen WG

| Active Acifluorifen (345 g/kg) | 34.6% |
|---|---|
| Microcel E | 25.6% |
| Morwet EFW | 3.2% |
| Morwet D-425 | 5.3% |
| Agrimer ATF | 1.0% |
| Sodium Citrate | 14.8% |
| ASP-NC | 14.1% |
| Residual Water | 1.5% |

No Sonics - 20 micron median particle size
Sonics - 17 micron median particle size Example 3: Bentazon WG

| Active Na Bentazon (400 g/kg) | 40.1% |
|---|---|
| Microcel E | 22.4% |
| Morwet EFW | 2.4% |
| Reax 45DTC | 6.5% |
| Agrimer ATF | 0.8% |
| Barden Clay | 26.3% |
| Residual Water | 1.5% |

No Sonics - 18 micron median particle size
Sonics - 18 micron median particle size Whereas particular embodiments of the invention have been described above for purposes of illustration, it will be appreciated by those skilled in the art that numerous variations of the details may be made without departing from the invention as described in the appended claims.

What is claimed is:

1. A method of making water-dispersible, granular formulation of a salt of a water soluble or hygroscopic pesticide comprising:

adsorbing a pesticidal effective amount of a salt of said water soluble or hygroscopic pesticide onto a highly adsorptive solid material which consists essentially of (i) filler/binder which is a delaminated kaolin clay, (ii) a synthetic calcium silicate carrier, and (iii) a dispersing agent which is a mixture of a lignosulfonic acid or a condensed sulfonated sodium salt with polyvinylpyrrolidone;

granulating, in the absence of a milling step, the composition by granulating means;

drying the granulated composition by drying means; and sizing the composition to remove any oversize fines.

2. The method of claim 1 wherein said pesticide is selected from the group consisting of plant growth regulators, insecticides, nematocides, herbicides, fungicides, miticides, pesticides, acaricides, algicides, bactericides and mollusicides.

3. The method of claim 2 wherein said pesticide is a plant growth regulator.

4. The method of claim 3 wherein said plant growth regulator is an N,N-dimethyl-piperidinium salt.

5. The method of claim 4 wherein said plant growth regulator is selected from the group consisting of 1,1-dimethyl-3,4-dehydropiperidinium bromide, 4-chloro-1,1-dimethylpiperidinium bromide, 1,1-dimethyl-hexahydropyridazinium bromide, and 1,1-dimethylpiperidinium chloride.

6. The method of claim 5 wherein said plant growth regulator is 1,1-dimethylpiperidinium chloride.

7. The method of claim 1 wherein said pesticide is sodium bentazon, sodium acifluorifen, the sodium salt of sethoxydim, the dimethyl amine salts of 2,4-D, difenzoquat methyl sulfate and mixtures thereof.

8. The method of claim 7 wherein said pesticide is sodium bentazon.

9. The method of claim 7 wherein said pesticide is sodium acifluorifen.

10. The method of claim 1 wherein said pesticide is present in an amount of about 5 to about 50 percent by weight.

11. The method of claim 1 wherein the highly absorbent solid and pesticide with granulation water are present in a ratio of about 0.1 to about 2.0 percent by weight.

12. The method of claim 1 wherein the formulation includes wetting agents.

13. The method of claim 12 wherein the wetting agents are surfactants.

14. The method of claim 13 wherein the wetting agents are selected from the group consisting of mixtures of alkyl carboxylates and sulfonated alkyl naphthalene and their sodium salts.

15. The method of claim 13 wherein said wetting agent is present in an amount of about 0.5 to about 10.0 percent by weight.

16. The method of claim 1 wherein the filler/binder is present in an amount up to about 60 percent by weight.

17. The method of claim 1 wherein said dispersing agent is present in an amount up to about 15.0%, by weight.

18. The method of claim 17 wherein said dispersing agent is present in an amount of about 0.5 to about 15.0%, by weight.

19. The method of claim 1 wherein said polyvinylpyrrolidone is preferably present in an amount up to 5.0%, by weight.

20. The method of claim 1 wherein the final granule particle size is a mixture of about <1.0 wt % +8 mesh, <3.0 wt % −30 mesh and <0.2 wt % −100 mesh.

21. The method of claim 1 wherein the median dispersed particle diameter size is about <40 micron after 5 minutes with dissolution without sonics.

22. The method of claim 1 wherein the loose bulk density is about 21 to 31 lb/cu ft or 0.34 to 0.50 g/ml.

23. The method of claim 1 wherein the packed bulk density is preferred to be about 23 to 33 lb/cu ft or 0.36 to 0.54 g/ml.

24. The method of claim 1 wherein the suspended final granules have a solids suspendability content of greater than about 50%.

25. The method of claim 24 wherein the active pesticide present is greater than about 90%.

26. A method of making a water-dispersible, granular pesticidal formulation comprising the sequential steps of:
  (a) adsorbing a pesticidal effective amount of a water-soluble or hygroscopic pesticide onto an unmilled highly adsorptive solid material which, consists essentially of (i) delaminated kaolin clay, (ii) a synthetic calcium silicate carrier, and (iii) a sulphonated dispersing agent; and thereafter
  (b) granulating the unmilled pesticide-containing solid material obtained according to step (a) to obtain a water-dispersible, granular pesticidal formulation having a median dispersed particle diameter size of less than 40 microns.

27. A method as in claim 26, which further comprises the step of (c) drying the granular pesticidal formulation obtained according to step (b).

28. A method as in claim 27 which further comprises the step of (d) sizing the dried granular pesticidal formulation obtained according to step (c) to remove fines.

* * * * *